United States Patent [19]
Ogawa et al.

[11] Patent Number: 5,985,329
[45] Date of Patent: Nov. 16, 1999

[54] PARTICULATE FOODS AND PHARMACEUTICALS COATED WITH WATER-SOLUBLE HEMICELLULOSE

[75] Inventors: Masanori Ogawa; Takehiko Ito, both of Hamakita; Chikako Ishigai, Hamamatsu; Hirokazu Maeda, Ibaraki-ken; Hitoshi Furuta, Sakai; Mitsuo Hattori, Ibaraki-ken, all of Japan

[73] Assignees: Freund Industrial Co., Ltd.; Fuji Oil Co., Ltd., both of Japan

[21] Appl. No.: 08/707,777

[22] Filed: Sep. 4, 1996

[30] Foreign Application Priority Data

Sep. 5, 1995 [JP] Japan ................................. 7-251959

[51] Int. Cl.⁶ ............................... A61K 9/36; A61K 9/14
[52] U.S. Cl. ....................... 424/494; 424/440; 424/489; 424/463; 424/474; 424/490; 426/89
[58] Field of Search ................................ 424/440, 489, 424/463, 474, 490, 494; 426/89

[56] References Cited

U.S. PATENT DOCUMENTS 4,927,649  5/1990  Antenucci ............................ 426/273

FOREIGN PATENT DOCUMENTS 0598920  6/1993  European Pat. Off. .

OTHER PUBLICATIONS

Patent Abstracts of Japan vol. 18, No. 410 Aug. 2, 1994.

*Primary Examiner*—Raj Bawa
*Attorney, Agent, or Firm*—Lorusso & Loud

[57] ABSTRACT

A coated product in the form of solid particles of a food or pharmaceutical wherein the particles are each coated with a water-soluble hemicellulose. The water-soluble hemicellulose has a viscosity in the range of from 50 to 1,000 mPa·s at 25° C. when dissolved in water in an amount of 10% by weight and has a reducing sugar content of 5% by weight or less and an amino acid content, as measured by assay with 2,4,6-trinitrobenezene sulfonic acid, of 1.0% by weight or less.

5 Claims, No Drawings

PARTICULATE FOODS AND PHARMACEUTICALS COATED WITH WATER-SOLUBLE HEMICELLULOSE

FIELD OF INVENTION

The present invention relates to a method for spray coating surfaces of small-size foods or pharmaceutical preparations in the form of powder, granules, pellets, tablets, spheres, capsules or the like and to materials coated by the spray coating.

TECHNICAL BACKGROUND

Food referred to as so-called health foods is in many cases prepared as small-size solid materials in the form of pellets, granules, tablets or the like, for example, from the point of view of easiness for management of amounts of food to be eaten and for the filling in containers or the like, unlike usual food people eats daily. These small-size foods are currently on the market in such a state that they are processed into products without coating their surfaces.

Some of these small-size foods are likely to become powder upon being subjected to an impact, when they have low surface strengths. Some small-size foods are prone for their active ingredients to deteriorate due to oxidation. Further, it sometimes causes to happen that foods smell undesirable or unpleasant.

It is desired, accordingly, that these small-size foods be coated at their surfaces with a coating layer of a polymer substance.

At the present time, however, no method of coating has been yet developed that can form a highly safe coating of a polymer substance on these small-size foods with high efficiency and at low costs.

On the other hand, a spray coating is known to the art that can form a coating of a polymer substance on the surfaces of small-size solid materials with high efficiency. The spray coating involves spraying small-size solid materials in a movable state with a solution of a polymer substance. It can be noted herein that the factor exerting the biggest influences on efficiency in preparation of products and costs of production thereof is a selection of a polymer substance to be sprayed in the form of a solution. Therefore, the selection of the polymer substance is the greatest problem to be solved.

As a result of extensive research and review, it has been found by the present inventors that polymeric substances, such as guar gum, gum traganth, xanthane gum, carrageenan, tamarind gum, locust bean gum, sodium carboxymethyl cellulose, sodium carboxymethyl starch and sodium alginate, are too high in viscosity in the form of an aqueous solution so that their spray coating characteristics are too poor to be practically applied. In order to make these natural polymer substances in the form of a solution having a relatively low viscosity appropriate for spray coating, it is necessary to make the polymer substance in the concentration as extremely low as 2% or lower. The solution having the polymer substance in such a low concentration suffers from the extremely great difficulty in the formation of a continuous coating layer having high durability. Further, the such solution requires a long period of time for drying a coating and it remarkably reduces efficiency in the preparation of products.

Further, natural polymer substances such as gum arabic, pullulan, gelatin and so on, are so high in viscosity that the products coated with such a natural polymer substance are prone to attach to each other, resulting in the formation of an aggregate with no commercial value.

On the other hand, for a pharmaceutical preparation, it is desired to develop a method of spray coating using an aqueous solution of a highly safe natural polymer substance. At the present time, however, no such a spray coating method has been developed yet.

The major object of the present invention is to provide a method for forming a highly safe coating of a natural polymer substance on surfaces of small-size foods or pharmaceutical preparations by spray coating with high production efficiency and at low production costs.

Another object of the present invention is to provide small-size foods and pharmaceutical preparations with a highly safe coating of a natural polymer substance coated on their surfaces.

Other objects, features and advantages will become apparent in the course of the description of the specification that follows.

DISCLOSURE OF INVENTION

In accordance with the present invention, there is provided a method of coating solid particles selected from foods and pharmaceutical preparations, comprising the step of spray coating said solid particles with an aqueous solution containing a water-soluble hemicellulose in an amount of 3% to 15% by weight while maintaining said solid particles in a moving state and while passing a gas therethrough, wherein said water-soluble hemicellulose has a viscosity in the range of from 50 to 1,000 mPa·s at 25° C. when dissolved in water in an amount of 10% by weight, and wherein said water-soluble hemicellulose has a reducing sugar content of 5% by weight or less and an amino acid content, as measured by the TNBS method, of 1.0% by weight or less.

In another aspect, the present invention provides a coated product comprising solid particles selected from foods and pharmaceutical preparations, and coatings of a water-soluble hemicellulose provided over the surface of each of said solid particles, said water-soluble hemicellulose having a viscosity in the range of from 50 to 1,000 mPa·s at 25° C. when dissolved in water in an amount of 10% by weight and said water-soluble hemicellulose having a reducing sugar content of 5% by weight or less and an amino acid content, as measured by the TNBS method, of 1.0% by weight or less. The "TNBS Method" is a conventional method for assay of free amine using 2,4,6-trinitrobenzene sulfonic acid as a reagent.

Raw materials to be treated by the method according to the present invention are small-size foods and pharmaceutical preparations which may be in the form of powder, granules, pellets, tablets, spheres, capsules or the like and have an average size of the products ranging from 0.1 to 40 mm, preferably from 0.2 to 30 mm.

It should be noted herein as a matter of course that the foods and pharmaceutical preparation to be used for the present invention are to be understood as containing foods or livestock feed to be fed to animals and a pharmaceutical preparation to be applied thereto, respectively, as well as foods to be eaten by the human being and the pharmaceutical preparations to be applied thereto.

The aqueous solution of a polymer substance for spraying (hereinafter referred to sometimes as a spraying solution) to be employed in the method according to the present invention is an aqueous solution of a water-soluble hemicellulose. The water-soluble hemicellulose to be used therein is a substance known to the art and it can be prepared by hydrolyzing water-insoluble plant fibers containing polysaccharides connected to a cellulose or the like in the plant under weakly acidic conditions into a water-soluble product (a water-soluble hemicellulose) and separating the resulting water-soluble product therefrom.

As the water-insoluble plant fibers, there may be mentioned, for example, those derived from oilseed such as soy bean, palm seed and the like and grains such as rice, wheat, corn and the like. It is particularly useful to employ bean-curd refuse obtained by removing a majority of fats and oil as well as protein from soy bean.

It is preferred that the hydrolyzation of the water-insoluble plant fibers is carried out under conditions that a pH of an aqueous solution of the water-insoluble plant fibers is close to the isoelectric point of the protein contained therein. For example, as the isoelectric point of soybean protein contained in bean-curd refuse is close to pH 4.5, it is preferred to subject the bean-curd refuse to the hydrolyzation at a pH range of froQ pH 3 to pH 7, preferably from pH 4 to pH 6.

The reason for effecting the hydrolyzation of plant fibers at a pH range close to the isoelectric point of the protein contained therein is because, if the hydrolyzation is carried out at a pH range coniderably lower than the isoelectric he protein contained therein, for example, when bean-curd refuse containing soybean protein is hydrolyzed under highly acidic conditions as low as pH 2 or less, the plant fibers are hydrolyzed to an excessive extent and the protein contained therein is caused to be eluted out together with the plant fibers. On the other hand, if the plant fibers containing protein is hydrolyzed under neutral or alkaline conditions where a pH range is considerably higher than the isoelectric point of the protein contained therein, the protein is caused to be solubilized and it is eluted out together with the plant fibers.

The temperature at which the hydrolyzation of the plant fibers containing protein is carried out may be a temperature range higher than ambient temperature, preferably from 80° C. to 130° C.

Details of the hydrolyzation is disclosed, for example, in Japanese Patent Unexamined Publication Nos. 4-325,058 and 3-236,759.

The aqueous hemicellulose solution contains polysaccharides consisting of galactose, arabinose, galacturonic acid, xylose, fucose, glucose, rhamnose and the like, among which the main ingredients are polysaccharides consisting of galactose, arabinose, galacturonic acid, and the like. Details of the analysis of the ingredients constituting the aqueous solution of water-soluble hemicellulose prepared by hydrolyzation are disclosed in the Japanese Patent Unexamined Publication No. 4-325,058. When the aqueous solution of the water-soluble hemicellulose is concentrated and dried, the water-soluble hemicellulose in a solid state can be produced.

As the aqueous water-soluble hemicellulose solution to be used for the present invention, it is advantageous to use a water-soluble hemicellulose containing a water-soluble hemicellulose having a relatively large molecular weight and the least possible amounts of monosaccharides and oligosaccharides. The molecular weight of the water-soluble hemicellulose to be used for the present invention may be the one that can provide viscosity ranging from 50 to 1,000 mPa·s, preferably from 80 to 200 mPa·s, when the hemicellulose in the form of a 10% by weight aqueous solution is measured for viscosity at 25° C. by a B-type rotation viscometer.

The amount of reducing sugars contained in the hemicellulose used for the present invention may be 5% by weight or less, preferably 3% by weight or less. If the amount of the reducing sugars exceeds 5% by weight, the hemicellulose will be discolored with time.

In the present specification, the content of the reducing sugars in the hemicellulose is as measured by Somogyi-Nelson method. In this measurement method, the amount of sugars having a free aldehyde group or a ketone group is determined in terms of the amount of galactose as a standard substance. The measured values contain the amount of the reducing sugars of the polysaccharides. However, when the molecular weight of the polysaccharides is high, the reducing sugars of the polysaccharide have little influence upon the amount of the reducing sugars of the monosaccharides and oligosaccharides. Further, although some oligosaccharides do not exhibit any reducing properties, the amount of such oligosaccharides is small, when the amount of the reducing sugars is small. Hence, the amount of the reducing sugars as measured by the above method can properly represent the total amount of the monosaccharides and oligosaccharides contained in the water-soluble hemicellulose.

As methods for the separation of the monosaccharides and the oligosaccharides from the hemicellulose, there may be mentioned, for example, (1) a method for separation thereof by adsorption to active carbon; and (2) a method for separation thereof by dissolving a monosaccharide and an oligosaccharide in an organic solvent such as ethyl alcohol or acetone and separating hemicellulose containing polysaccharides having a large molecular weight as an undissolved material.

The water-soluble hemicellulose contains water, ash, protein, amino acids and the like, in addition to the monosaccharides and oligosaccharides. Table below shows properties of water-soluble hemicelluloses as referred to therein as Sample Nos. 1 to 4.

In the Table below, the amounts of the reducing sugars are represented as an amount of galactose as a standard substance, which is calculated from the values measured by the Somogyi-Nelson method. It is found as a result that the amounts of the reducing sugars nearly correspond to the amounts of the monosaccharides and oligosaccharides in the hemicellulose.

The amounts of amino acids indicated in the Table below are obtained by measurement using TNBS method. The TNBS method is the method reported by okuyama et al. which is a method using sodium 2,4,6-trinitrobenzene sulfonate (Protein, Nucleic Acids & Enzymes: vol. 18, page 1154 (1973)) and which calculates the amount of amino acids and peptides as an amount of sodium glutamate as a standard substance.

The evaluation of adhesion indicated in the Table below represents the results of evaluation on sticky. properties of the water-soluble hemicellulose. In the Table, reference symbol ⊚ indicates the hemicellulose having no sticky properties; reference symbol ○ indicates the hemicellulose having no substantial sticky degree of sticky properties; and reference symbol X indicates the emicellulose having a substantial degree of sticky properties.

TABLE

| SAMPLE NOS. | WATER CONTENTS (% BY WEIGHT) | CRUDE PROTEIN (% BY WEIGHT) | CRUDE ASH (% BY WEIGHT) | VISCOSITY OF A 10% BY WEIGHT SOLUTION (mPa/s, 25° C.) | REDUCING SUGARS (% BY WEIGHT) | AMINO ACIDS (% BY WEIGHT) | EVALUATION OF ADHESION |
|---|---|---|---|---|---|---|---|
| 1 | 6.0 | 3.1 | 4.4 | 95.7 | 1.69 | 0.77 | ⊚ |
| 2 | 5.9 | 6.7 | 6.1 | 92.0 | 2.33 | 0.96 | ○ |
| 3 | 3.7 | 5.3 | 6.8 | 86.0 | 1.42 | 1.51 | x |
| 4 | 3.2 | 6.6 | 4.4 | 160.0 | 1.83 | 1.08 | x |

The values measured as the amount of the amino acids by the TNBS method include the amounts of peptides and proteins in addition to the amino acids. It can be noted herein, however, that the peptides and proteins having large molecular weights do not exert any great influence upon the measured values so that the values measured as the amount of the amino acids are close to an actual amount of the amino acids. It can also be noted that the amount of the amino acids in the water-soluble hemicellulose to be used for the present invention represents an amount of amino acids measured for the water-soluble hemicellulose by the TNBS method.

When the amount of the amino acids in the water-soluble hemicellulose is 1.0% by weight or less, the hemicellulose causes no problem with adhesive properties and can be advantageously applied to the present invention.

As processes for removal of the amino acids from the water-soluble hemicellulose, there may be mentioned, for example, (1) a process comprising bringing an aqueous hemicellulose solution into contact with active carbon; (2) a process comprising bringing an aqueous hemicellulose solution into contact with an ion exchange resin; and (3) a process comprising bringing an aqueous hemicellulose solution into contact with an organic solvent such as ethanol or acetone. In the process (1) above, the amino acids are adsorbed onto the active carbon and then removed from the aqueous hemicellulose solution; in the process (2) above, the amino acids are adsorbed onto the ion exchange resin and then removed therefrom; and in the process (3) above, the amino acids are extracted into the organic solvent and then removed therefrom.

The water-soluble hemicellulose in the form of powder may be prepared by dissolving the hemicellulose in a concentration of from 2% to 10% by weight adjusted so as to contain monosaccharides and oligosaccharides in an amount of 5% by weight or less and amino acids in an amount of 1% by weight or less in water and evaporating the water from the resulting aqueous solution and concentrating it to a solution containing the hemicellulose in the concentration of nearly 15% by weight. The concentrated solution was then dried with a spray dryer.

The powdery hemicellulose prepared in the manner as described hereinabove is soluble in water and it has a viscosity of from 50 to 1,000 mPa·s, preferably from 80 to 200 mPa·s, at 25° C. in the form of an aqueous solution containing it in an amount of 10% by weight. It further contains reducing sugars in an amount of 5% by weight or less, preferably 3% by weight or less and amino acids in an amount of 1% by weight or less, preferably 0.8% by weight or less, when measured by the TNBS method. An average particle size of the powdery hemicellulose is usually from 50 to 60 μm. The powdery hemicellulose may be filled in containers, stored and transported.

The spraying solution to be used for the spray coating method according to the present invention may be prepared by dissolving the powdery hemicellulose in water. The concentration of the hemicellulose in the aqueous solution may range from 2% to 20% by weight, preferably from 3% to 15% by weight. The spraying solution is found superior in spraying characteristics because it causes no sagging or trailing in the form of string or thread when spraying. If the spraying solution causes such sagging or trailing, it is not desired because it may cause problems that the sprayed solution blown through the nozzle may not be atomized, thereby allowing no uniform coating to be formed on a substrate and causing the coated products to stick to each other.

In forming a hemicellulose coating on the surfaces of the small-size foods or pharmaceutical preparations (hereinafter referred to sometimes merely as substrate), the substrate are held in a moving state and sprayed with a spraying solution through a spray nozzle under the flow of gases (in a usual case, air). Upon spraying, the spraying solution is caused to attach to the surface of the moving substrate and allowed to dry by the aid of the flowing gases, thereby resulting in the formation of a hemicellulose coating thereon. The temperature of the gases may range from 30° C. to 100° C., preferably from 40° C. to 90° C.

As a spraying device, there may be employed, for example, a spray gun for spraying the spraying solution together with gases such as air or an airless spray gun.

To the spraying solution, there may be added a plasticizer, a coating aid, a pigment, a coloring agent, a dispersing agent, a solvent, a flavoring agent, a preservative, an anti-foaming agent and the like. The spraying solution may also contain other natural polymer substances.

The temperature for the spray coating according to the present invention, that is, the temperature of the moving substrate to be sprayed, may range from 30 to 100° C., preferably from 60 to 90 ° C. The temperature for the spray coating can be adjusted by the temperature of the gases. The viscosity of the spraying solution at the outlet of the spray nozzle may range from 10 to 500 mPa·s, preferably from 20 to 200 mPa·s. The viscosity of the spraying solution may be adjusted on the basis of the temperature thereof and the concentration of the hemicellulose.

The spray coating method according to the present invention may include four processes as will be described hereinbelow.

Process I:

An appropriate amount of the substrate is charged in a container with a horizontal rotary shaft mounted thereon and held in a movable state in the container by rotating the container. The substrate is sprayed with the spraying solution while drying gases (in usual cases, air) are introduced into the container via a through hole formed in the peripheral wall of the container.

This process enables the substrate to be coated for a short coating period of time and with high efficiency because the drying gases are allowed to pass through the substrate in a moving state.

The size of the container to be employed for this process may be such that the diameter thereof ranges from 20 cm to 170 cm. The spraying speed of the spraying solution may range generally from 3 to 500 ml per minute and the amount of the gases to be introduced may range from 0.3 to 50 cubic meters per minute and the amount of the substrate to be charged may be in the range of from 0.3 to 400 kilograms. The processing time may range from 35 minutes to 240 minutes and the speed of revolutions of the container may be in the range of from 5 to 30 rpm.

A device to be employed for this process may include, for example, a coating device such as trade names HI-COATER and AQUA COATER, each manufactured by Freund Industrial Co., Ltd.

Process II:

This process is to spray the substrate held in a flowing state in a rising gas stream.

For carrying out this process, there may be employed, for example, a fluidized bed device of a tower type having a gas dispersing plate at its bottom.

For the fluidized bed device, the tower diameter may range from approximately 13 cm to 160 cm. General operational conditions for operating the fluidized bed device may be such that the size of the substrate may be in the range of from 0.5 mm to 3 mm; the substrate may be fed in the amount ranging from 0.3 kilograms to 300 kilograms; the spraying speed of the spraying solution may range from 3 to 600 ml per minute; and the drying gases may be fed in an amount of from 0.5 to 100 cubic meters per minute.

As the fluidized bed device is large in drying capacity, the spray coating can be carried out with high efficiency.

As the fluidized bed device, there may be employed, for example, a fluidized bed device called trade name FLO-COATER (manufactured by Freund Industrial Co., Ltd.).

Process III:

This process comprises spraying the substrate with the spraying solution while blowing the gases upwardly onto the substrate rotating with the aid of the action by a rotor disk and fluidizing a portion of the substrate.

A device to be employed for this process may be a fluidized bed device with a rotor disk disposed at the bottom portion of the fluidized bed. The device can sustain a portion of the substrate in a rotating state by the rotation of the rotor disk and the rest of the substrate in a fluidized state.

As such a device, there may be mentioned, for example, fluidized bed devices having trade names SPIR-A-FLOW and Rotor Container (each being manufactured by Freund Industrial Co., Ltd.)

Process IV:

This process comprises spraying the substrate with the spraying solution in such a state that the substrate is subjected to planetary movement on a rotating disk disposed in a container and the gases are fed to the inside of the container.

In the spray coating method according to the present invention, the small-size foods and pharmaceutical preparations can be coated directly thereonto or spray coated on products precoated by spray coating. The spray coating method according to the present invention can provide the surfaces of the small-size foods and pharmaceutical preparations with a non-sticky hemicellulose coating having a film thickness ranging from approximately 10 to 50 μm with high efficiency.

EXAMPLES

Example 1

To 5 kilograms of raw bean-curd refuse obtained in the step of producing soybean protein was added a two-fold amount, i.e. 10 liters, of water, and the mixture was adjusted to pH 4.5 with hydrochloric acid. The resulting mixture was then subjected to hydrolyzation at 120° C. for 1.5 hours and the resulting product was centrifuged at 10,000 rpm for 30 minutes, thereby separating a supernatant from precipitated materials. The supernatant separated was then treated through an activated carbon column, thereby adsorbing monosaccharides, oligosaccharides and amino acids thereonto. Thereafter, the resulting aqueous solution was concentrated and dried to yield 260 grams of powdery, water-soluble hemicellulose. The analysis of the hemicellulose is as follows:

Water content: 6.0% by weight
Crude protein: 3.1% by weight (in a dry state)
Crude ash: 4.4% by weight (in a dry state)
reducing sugars: 1.69% by weight
Amino acids: 0.77% by weight An aqueous solution containing water-soluble hemicellulose in an amount of 10% by weight indicated viscosity of 95.7 mPa·s, when measured at 25° C. with a B-type rotation viscometer.

The powdery, water-soluble hemicellulose was dissolved in water, thereby yielding an aqueous solution containing hemicellulose in the concentration of 9.0% by weight.

In a coating device (Model: HI-COATER HC-48N; manufactured by Freund Industrial Co., Ltd.) was charged 3.5 kilograms of lactose tablets each having a diameter of 8 mm. While feeding air into the device, the resulting aqueous hemicellulose solution was sprayed into the device through a spray nozzle.

The coating device comprised a lateral container provided with a number of through holes on a peripheral wall thereof and disposed so as to rotate about a substantially horizontal axis and a spray nozzle disposed within the container. The substrate was charged in the container, air was fed at a central portion of the container, and the spraying solution was fed to the spray nozzle. The air fed within the container was discharged outside via the through holes disposed on the peripheral wall of the container.

The diameter of the container for the coating device used in this example was set to be 48 cm.

The operational conditions of the coating device were as follows: temperature of the air fed, 65° C.; spraying pressure at the nozzle, 3.0 kg per square centimeter; speed of spraying, 20 ml per minute; amount of air fed, 2.8 cubic meter per minute; and speed of revolutions of the container, 15 rpm.

By subjecting the substrate to spray coating for 120 minutes in the manner as described hereinabove, there was yielded tablets product (coated products), each having a hemicellulose coating formed on the surface thereof. In this case, the amount of the hemicellulose coating was 6% by weight with respect to the tablet as a raw material.

It can be noted herein that the operation of the spray coating method could be conducted smoothly and the spraying solution flown through the spray nozzle caused neither sagging nor trailing in the form of a string or thread. Further, the coated products did not adhere to each other.

The coated products yielded in the above-mentioned manner were subjected to disintegration tests by first fluid according to the Pharmacopoeia of Japan. As a result, the raw tablets were disintegrated in 2 minutes 15 seconds, while the coated product was disintegrated in 5 minutes 17 seconds.

Comparative Example 1

The operations were conducted in substantially the same manner as in Example 1, with the exception that the aqueous solution of the water-soluble hemicellulose was replaced by an aqueous solution containing 12% by weight of gum arabic or a 8% by weight water-containing ethanol solution of casein (water-containing amount: 20% by volume). As a result, it was found that the aqueous solution of gum arabic is too high in adhesion to smoothly effect spray coating.

On the other hand, the water-containing ethanol solution of casein enabled a good operation for spray coating and provided a coated product that looked favorable in appearance. As a result of disintegration tests according to the Pharmacopoeia of Japan, however, it was found inappropriate as a gastric-soluble coating because the coated product was not disintegrated in 60 minutes.

Comparative Example 2

The operations were conducted in substantially the same manner as in Example 1, with the exception that a water-soluble hemicellulose was used which had viscosity of 56.4 mPa·s at 25° C. in the form of an aqueous solution containing hemicellulose in an amount of 10% by weight and contained amino acids in an amount of 1.3% by weight. As a result, it was found that the resulting coated products were too sticky and they adhered to each other.

Example 2

As a coating device, there was employed a fluidized bed coating device having an inner tower diameter of 13.5 cm (Model: FLO-COATER FL-mini Type; manufactured by Freund Industrial Co., Ltd.). Into the coating device, air for fluidizing was fed in an amount of 0.5 to 0.8 cubic meter per minute from the bottom portion of the fluidized bed, thereby sustaining the substrate in a fluidized state. To the substrate was fed an aqueous solution containing 5% by weight of water-soluble hemicellulose and 2% by weight of glycerin, as a spraying solution, in an amount of 2.5 ml per minute through an atomizing nozzle, together with compressed air, thereby subjecting the substrate to spray coating.

As the substrate, there were used spherical sucrose granules having particle sizes of from 590 to 710 $\mu$m (Nonpareil-103; produced by Freund Industrial Co., Ltd.).

As the water-soluble hemicellulose, there was used hemicellulose having viscosity of 88.7 mPa·s at 25° C. in the form of an aqueous solution containing hemicellulose in an amount of 10% by weight and containing reducing sugars in an amount of 1.8% by weight and amino acids in an amount of 0.9% by weight.

The operational conditions of the coating device were as follows: temperature of the air for fluidizing, 90° C.; and spraying pressure at the nozzle, 1.5 kg per square centimeter.

A coated product with the surface thereof coated with a coating of hemicellulose was yielded by carrying out spray coating for 40 minutes in the manner as described hereinabove. The amount of the hemicellulose coating formed on the surface of the coated product was 2.4% by weight with respect to the spherical sucrose granules used as a raw substrate.

It can be noted herein that the operation of the spray coating method could be conducted smoothly and the spraying solution flown through the spray nozzle caused neither sagging nor trailing in the form of a string or thread. Further, the coated products did not adhere to each other.

The coated products yielded in the above-mentioned manner were subjected to disintegration tests according to the Pharmacopoeia of Japan. As a result, the non-coated product was disintegrated in 7 seconds, while the coated product was disintegrated in 12 seconds.

Example 3

The substrate as used in Example 2 above in the amount of 5 kg was spray coated with a spraying solution consisting of an aqueous solution containing 9% by weight of the water-soluble hemicellulose as used in Example 2 above and 1% by weight of glycerin by the aid of a fluidized bed coating device (FLO-COATER Model FLO-5 Type; manufactured by Freund Industrial Co., Ltd.) as a coating device. The spray coating was carried out while feeding air for fluidizing at the temperature of 80° C. and the spraying pressure of 3.0 kg per cubic meter at the spray nozzle.

A coated product with the surface thereof coated with a coating of hemicellulose was yielded by carrying out spray coating for 40 minutes in the manner as described hereinabove. The amount of the hemicellulose coating formed on the surface of the coated product was 2.9% by weight with respect to the spherical sucrose granules used as a raw substrate.

It can be noted herein that the operation of the spray coating method could be conducted in a smooth manner and the spraying solution flown through the spray nozzle caused neither sagging nor trailing in the form of a string or thread. Further, the coated products did not adhere to each other.

The coated products yielded in the above-mentioned manner were subjected to disintegration tests according to Pharmacopoeia of Japan. As a result, the non-coated product was disintegrated in 7 seconds, while the coated product was disintegrated in 12 seconds.

Example 4

The spherical sucrose granules in the amount of 600 grams, as used in Example 2 above, were spray coated with the spraying solution as used in Example 3 above by the aid of a fluidized bed coating device (SPIR-A-FLOW Model SFC-Mini Type; manufactured by Freund Industrial Co., Ltd.) with a rotor disk disposed at its bottom portion so as to rotate the substrate by the rotation of the rotor disk.

The inner diameter of the fluidizing tower of the fluidized bed device was 15.5 cm and the number of revolutions of the rotor was 400 rpm.

The spray coating was carried out by blowing fluidizing air at the temperature of 70° C. and at the feed speed of 0.8 to 1.0 cubic meter per minute and feeding the spraying solution in an amount of 2 ml per minute through a spraying nozzle at the spraying pressure of 3.0 kg per cubic centimeter.

A coated product with the surface thereof coated with a coating of hemicellulose was yielded by carrying out spray coating for 80 minutes in the manner as described hereinabove. The amount of the hemicellulose coating formed on the surface of the coated product was 2.3% by weight with respect to the spherical sucrose granules used as a raw substrate.

It can be noted herein that the operation of the spray coating method could be conducted smoothly and the spraying solution flown through the spray nozzle caused neither sagging nor trailing in the form of a string or thread. Further, the coated products did not adhere to each other.

The coated products yielded in the above-mentioned manner were subjected to disintegration tests according to the Pharmacopoeia of Japan. As a result, the non-coated product was disintegrated in 7 seconds, while the coated product was disintegrated in 12 seconds.

Comparative Example 3

The operations were carried out in substantially the same manner as in Example 3 above, with the exception that pullulan was used in place of the water-soluble hemicellulose. As a result, it was found that the coated products were too sticky and they adhered to each other into aggregates.

What is claimed is:

1. A particulate product comprising solid particles coated with a water-soluble heimcellulose and having an average size of 0.1 to 40 mm, said particles selected from the group consisting of foods and pharmaceutical preparations, said water-soluble hemicellulose having a viscosity in the range of from 50 to 1,000 mPa·s at 25° C. when dissolved in water in an amount of 10% by weight and said water-soluble hemicellulose having a reducing sugar content of 5by weight or less and an amino acid content, as measured by assay with 2,4,6-trinitrobenzene sulfonic acid, of 1.0% by weight or less.

2. A coated product as claimed in claim 1 wherein said solid particles have an average size of 0.2 to 30 mm.

3. A particulate product as claimed in claim 1 produced by a process comprising:

spray coating said solid particles with an aqueous solution containing the water-soluble iemicellulose in an amount of 3% to 15% by weight while maintaining said solid particles in a moving state and while passing a gas therethrough.

4. A coated product as claimed in claim 3 wherein said solid particles are in the form of power, granules, pellets, tables, spheres or capsules.

5. A coated product as claimed in claim 1 wherein said solid particles are in the form of powder, granules, pellets, tablets, spheres or capsules.

* * * * *

UNITED STATES PATENT AND TRADEMARK OFFICE
CERTIFICATE OF CORRECTION

PATENT NO. : 5,985,329
DATED : November 16, 1999
INVENTOR(S) : Ogawa *et al.*

It is certified that error appears in the above-identified patent and that said Letters Patent is hereby corrected as shown below:

Claim 1, line 6, change "25°C.when" to --25°C when--;

Line 9, change "of5by" to --of 5% by--.

Claim 3, line 4, change "iemicellulose" to --hemicellulose--.

Signed and Sealed this

Twenty-second Day of May, 2001

Attest:

NICHOLAS P. GODICI

*Attesting Officer*     *Acting Director of the United States Patent and Trademark Office*